(12) United States Patent
Kim

(10) Patent No.: US 8,123,576 B2
(45) Date of Patent: Feb. 28, 2012

(54) CONNECTING STRUCTURE OF SNAP ELECTRODE AND ELECTRIC WIRE

(75) Inventor: Se-Jin Kim, Suwon-Si (KR)

(73) Assignee: Daehan Medical Systems Co., Ltd., Siheung-Si (KR)

( * ) Notice: Subject to any disclaimer, the term of this patent is extended or adjusted under 35 U.S.C. 154(b) by 140 days.

(21) Appl. No.: 12/769,710

(22) Filed: Apr. 29, 2010

(65) Prior Publication Data

US 2011/0201913 A1    Aug. 18, 2011

(30) Foreign Application Priority Data

Feb. 18, 2010  (KR) .................. 10-2010-0014646

(51) Int. Cl.
*H01R 9/22* (2006.01)
(52) U.S. Cl. ........... 439/909; 439/668; 607/37; 607/119
(58) Field of Classification Search .................. 439/668, 439/909; 607/37, 119
See application file for complete search history.

(56) References Cited

U.S. PATENT DOCUMENTS

| | | | |
|---|---|---|---|
| 4,207,904 A * | 6/1980 | Greene | 607/152 |
| 5,232,383 A * | 8/1993 | Barnick | 439/859 |
| 5,427,096 A * | 6/1995 | Bogusiewicz et al. | 600/396 |
| 6,064,901 A * | 5/2000 | Cartmell et al. | 600/372 |
| 6,745,082 B2 * | 6/2004 | Axelgaard | 607/142 |
| 7,081,026 B2 * | 7/2006 | Schwarz | 439/729 |
| 7,245,957 B2 * | 7/2007 | Rowe et al. | 600/391 |
| 7,445,522 B2 * | 11/2008 | Burnes et al. | 439/725 |

* cited by examiner

*Primary Examiner* — Truc Nguyen
(74) *Attorney, Agent, or Firm* — NSIP Law

(57) ABSTRACT

A structure of electrically connecting a snap electrode for medical purposes is easily attached/detached to/from various monitoring pads attached to a human body to measure electrocardiogram (ECG), electromyogram (EMG), brain wave and nervous system signals and electrically connected to medical equipment, to an electric wire using a pressing method instead of welding. The connecting structure of a snap electrode and an electric wire includes a body having a convex portion, which is formed on the top of the body and has a groove formed on the circumference thereof, in which a combining part is fitted, and the combining protrusion having a ring shape and including a predetermined number of elastic fixing pieces protruded from the inner side thereof and a pair of first pressing pieces protruded from one side thereof and combined with an electric wire. A combining protrusion of a pad is inserted into the body.

10 Claims, 6 Drawing Sheets

CONNECTING STRUCTURE OF SNAP ELECTRODE AND ELECTRIC WIRE

CROSS-REFERENCE TO RELATED APPLICATION(S)

This application claims the benefit under 35 U.S.C. §119 (a) of Korean Patent Application No. 10-2010-0014646, filed on Feb. 18, 2010, in the Korean Intellectual Property Office, the entire disclosure of which is incorporated herein by reference for all purposes.

BACKGROUND

1. Field

The following description relates to a structure of electrically connecting a snap electrode for medical purposes, which is easily attached/detached to/from various monitoring pads attached to a human body to measure electrocardiogram (ECG), electromyogram (EMG), brain wave and nervous system signals and electrically connected to medical equipment, to an electric wire using a pressing method instead of welding.

2. Description of Related Art

An action current of a muscle, which represents an action potential of the muscle, is referred to as electromyogram, and excitement of the heart muscle occurs in the venous sinus and proceeds to an atrium and a ventricle. If the excitement is induced to an ammeter (electrocardiograph) at arbitrary two points, the action current of the heart is represented as a graph. This graph is an electrocardiograph (ECG), which is very important to diagnose cardiac disorders.

FIGS. 1 and 2 illustrate a conventional connecting structure of a snap electrode 10 and an electric wire 12 for measuring ECG and EMG.

As shown in FIG. 1, a combining protrusion 14, which is inserted into the snap electrode 10 to be combined with the snap electrode 10, is formed at the center of one side of a pad 13 attached to a human body, and the snap electrode 10 electrically connected to monitoring equipment through the electric wire 12 is combined with the combining protrusion 14.

As shown in FIG. 2, the electric wire 12 is welded to the body 15 of the snap electrode 10 using a material such as lead, and the snap electrode 10 is covered with a case 11 injection-molded using a synthetic resin that is not harmful to the human body. A portion protruded from the top of the body 15 of the snap electrode 10 is formed to secure a space in which the combining protrusion 14 formed on the pad 13 shown in FIG. 1 is mounted when the combining protrusion 14 is inserted into the body 15 of the snap electrode 10.

The aforementioned conventional electric wire connecting structure connects the snap electrode 10 and the electric wire 12 to each other through welding using a metal such as lead, and thus the metal such as lead can harm the human body and the electric wire 12 can be easily detached from the snap electrode 100 due to poor welding. Furthermore, the electric wire 12 is welded to the body 15 of the snap electrode 10 every time the snap electrode is use, and thus productivity is decreased.

Moreover, there is a trend toward restraining the snap electrode from welding using a material such as lead to construct medical equipment by a low.

SUMMARY

Accordingly, embodiments have been made in view of the above-mentioned problems occurring in the prior art, and it is an object to provide a connecting structure of a snap electrode for medical purposes and an electric wire, which can securely connect the electric wire to the snap electrode without fixing the electric wire to the snap electrode through welding using a material such as lead and easily assemble the electric wire and the snap electrode to improve productivity.

To accomplish the above object, according to embodiments, there is provided a connecting structure of a snap electrode for medical purposes and an electric wire, which includes: a body on which a convex portion having a groove formed on the circumference thereof, in which a combining part is fitted, is formed; a base having a protrusion housing formed at the center thereof and spring slits formed at both sides of the protrusion housing, into which press springs are inserted; and the combining part having a ring shape and including a predetermined number of elastic fixing pieces protruded from the inner side thereof and a pair of first pressing pieces protruded from one side thereof and combined with the electric wire.

The elastic fixing pieces may be bent upward at a predetermined angle or curved with a predetermined curvature.

The connecting structure may further include second pressing pieces formed at one side of the combining part to press and fix a coat of the electric wire.

The connecting structure may further include a case covering the body such that the body and a wire connecting part are not exposed to the outside.

Upper cut faces of the spring slits formed at both sides of the protrusion housing may be cut in a curved shape.

Embodiments constructed as above press-fix the electric wire to a ring-shaped combining part and combine the combining part with a protrusion of the body of the snap electrode without fixing the electric wire to the snap electrode through welding using a material such as lead so as to securely connect the electric wire to the snap electrode and easily assemble the electric wire and the snap electrode to improve productivity.

Other features and aspects will be apparent from the following detailed description, the drawings, and the claims.

Figure 1:
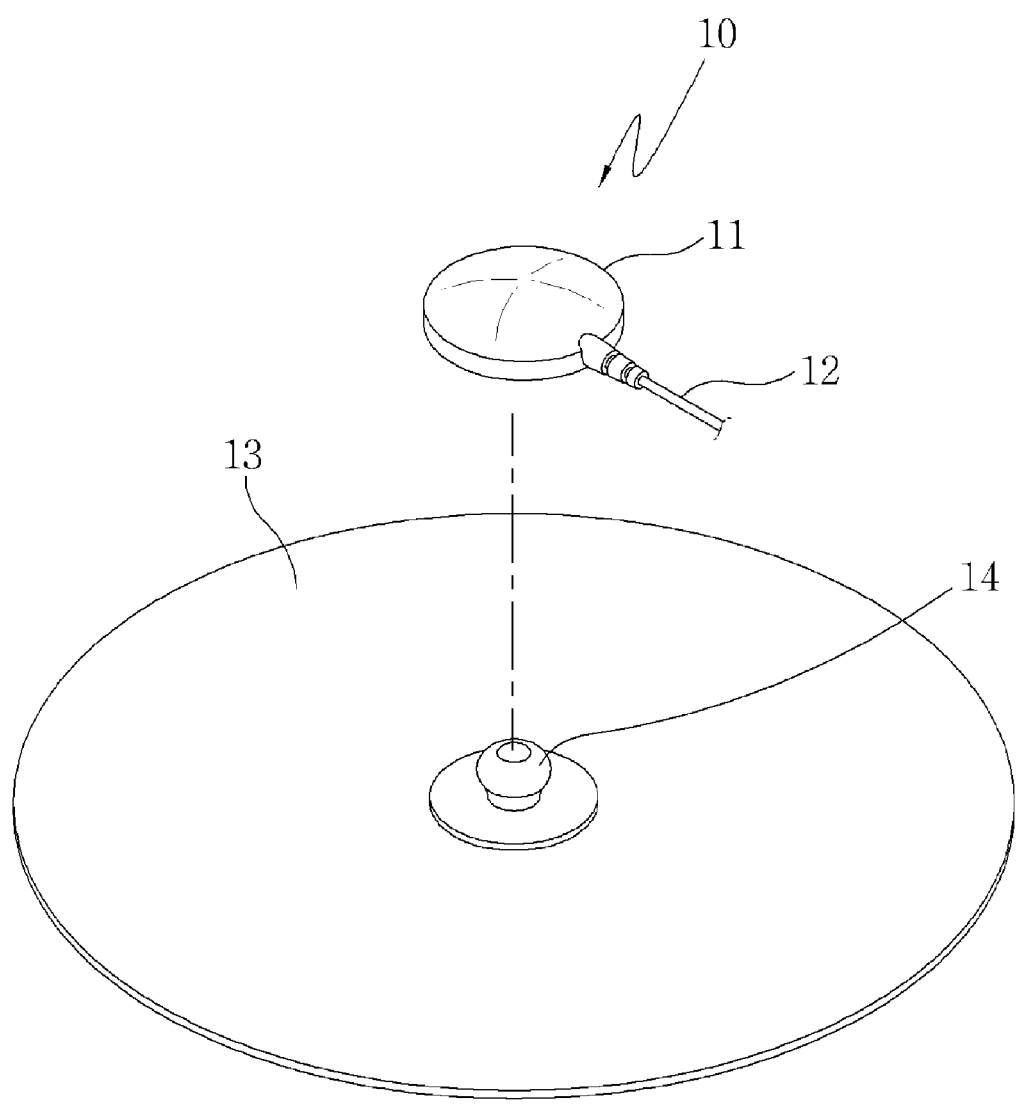
FIG. 1 is a perspective view showing a conventional connecting structure of a snap electrode and an electric wire.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION OF THE PREFERRED EMBODIMENT

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of well-known functions and constructions may be omitted for increased clarity and conciseness.

Hereinafter, embodiments will be described in detail by explaining preferred embodiments with reference to the attached drawings.

Figure 3:
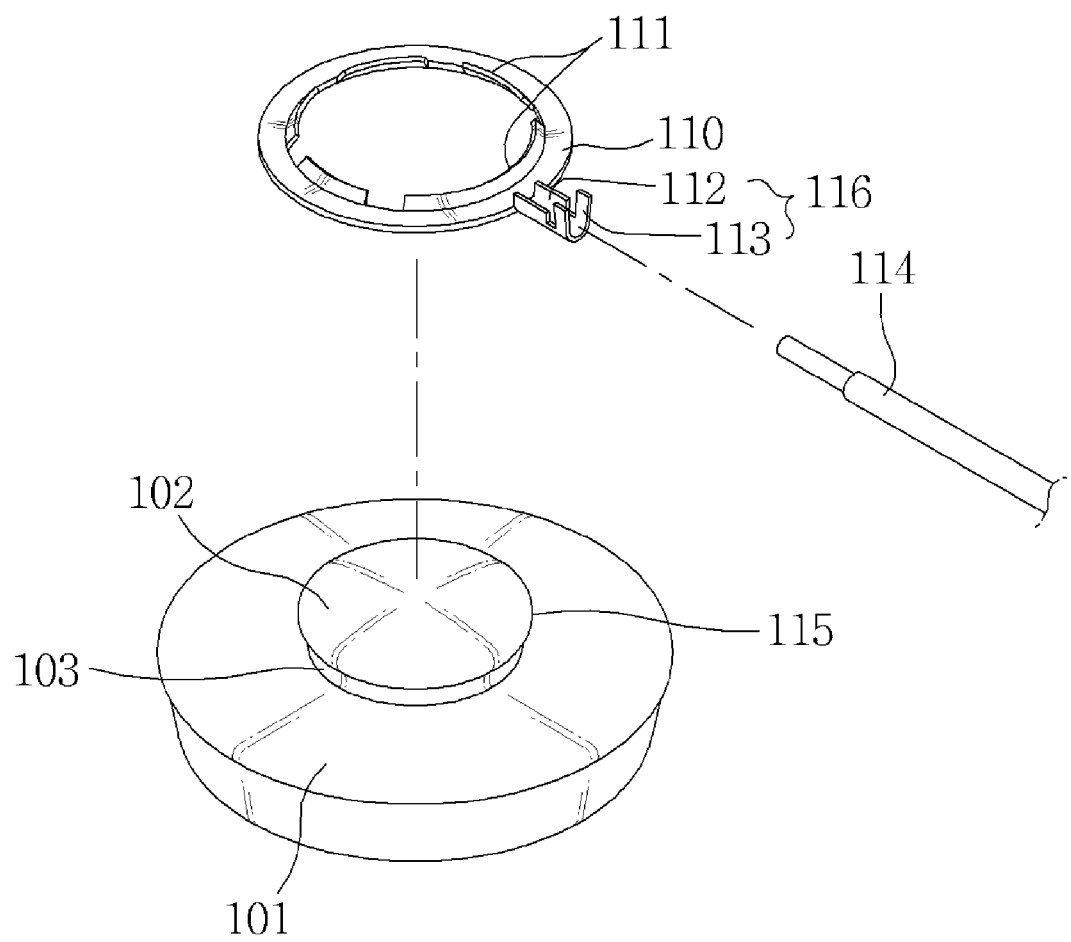
FIG. 3 is an exploded perspective view showing a connecting structure of a snap electrode and an electric wire according to an embodiment.
Figure 4:
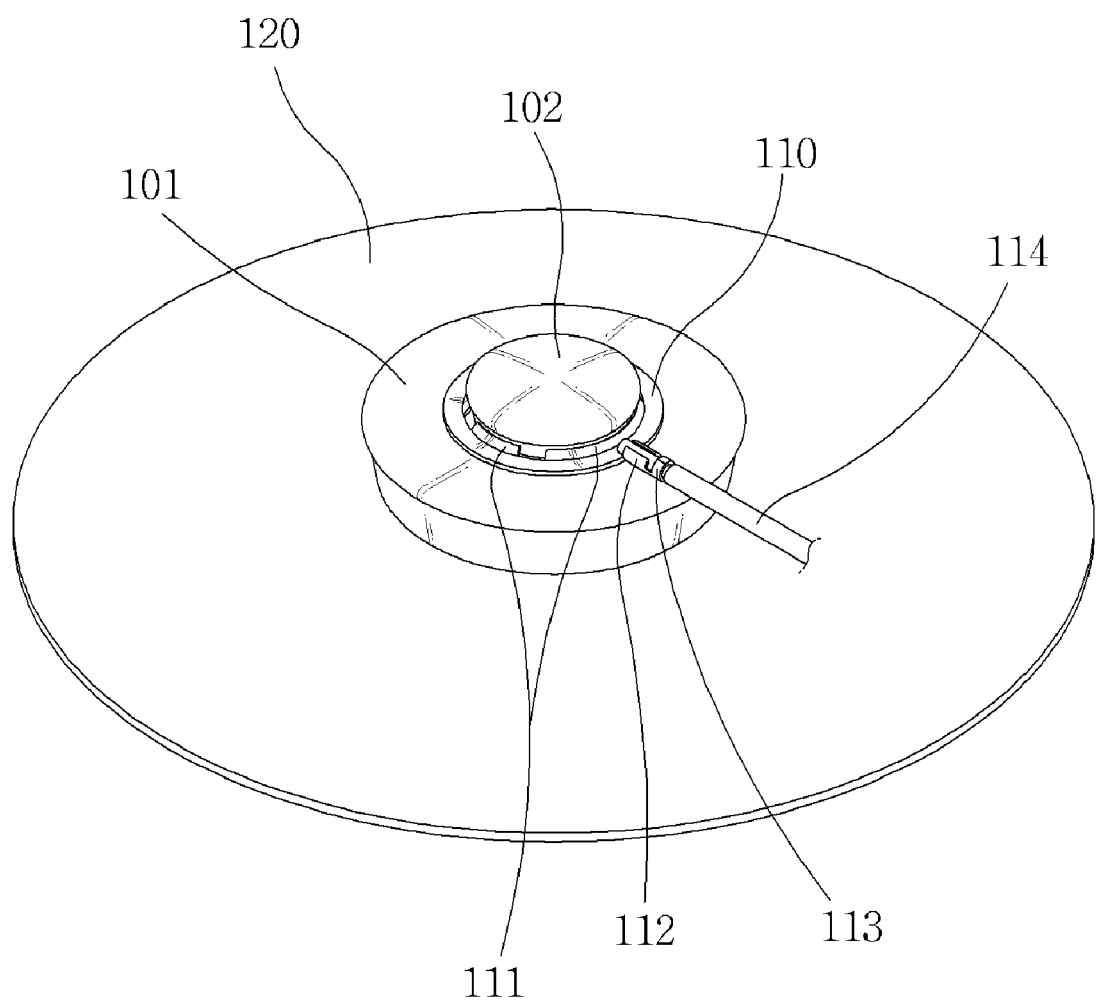
FIG. 4 is a perspective view showing the connecting structure of the snap electrode and the electric wire according to an embodiment.

FIG. 3 is an exploded perspective view showing a connecting structure of a snap electrode and an electric wire according to an embodiment and FIG. 4 is a perspective view showing the connecting structure of the snap electrode and the electric wire according to an embodiment. The connecting structure of the snap electrode and the electric wire according to an embodiment includes a body 101 having a convex portion 102, which is formed on the top of the body 101 and has a groove 103 formed on the circumference thereof, in which a combining part 110 is fitted, and the combining protrusion 110 having a ring shape and including a predetermined number of elastic fixing pieces 111 protruded from the inner side thereof and a pair of first pressing pieces 112 protruded from one side thereof and combined with an electric wire 114. A combining protrusion of a pad 120 is inserted into the body 101.

The pad 120 is attached to a human body to measure ECG, EMG, brain wave and nervous system signals. Since the pad 120 is frequently changed and used, the snap electrode is formed at an end of the electric wire 114 which is electrically connected to monitoring equipment to be easily attached/detached to/from the pad 120.

Referring to FIG. 3, the snap electrode includes the body 101 and the combining part 110 for electrically connecting the electric wire 114 to the body 101.

The body 101 of the snap electrode has a disc shape and includes the convex portion 102 projected from the top of the body 101. A mounting space (not shown) into which the combining protrusion 14 projected from the pad 13, shown in FIG. 1, is inserted and fixed is formed at the bottom of the body 101. To form this mounting space, the top of the body 101 is projected to form the convex portion 102.

The groove 103 is formed on the circumference of the convex portion 102 such that the ring-shaped combining part 110, which will be described later, is fitted in the groove 103 and combined with the body 101.

As shown in FIG. 3, the combining part 110 has a ring shape and includes the pair of first pressing pieces 112 and a pair of second pressing pieces 113, which are protruded from one side of the combining part 110. The fixing pieces 111 are formed on the inner side of the combining part 110.

The elastic fixing pieces 111 is molded such that the elastic fixing pieces 111 are bent upward at a predetermined angle or curved upward with a predetermined curvature, and thus the elastic fixing pieces 111 are stopped by a retaining projection 115 of the convex portion 102 when the combining part 110 is combined with the convex portion 102 of the body 101 so as to be securely fixed to the body 101.

That is, since the fixing pieces 111 have elasticity, the fixing pieces 111 are elastically deformed such that the convex portion 102 is smoothly fitted in the combining part 110 when the combining part 110 is combined with the convex portion 102, and then the fixing pieces 111 are elastically restored to be stopped by the retaining projection 115 to securely fix the combining part 110 to the body 101, as shown in FIG. 4.

A wire connecting part 116 is protruded from one side of the combining part 110 and includes the pair of first pressing pieces 112 and the pair of second pressing pieces 113, as shown in FIG. 3.

The electric wire 114 is generally composed of an electrically conductive metal wire and a synthetic resin coat covering the metal wire. The metal wire is disposed between the first pressing pieces 112, the first pressing pieces 112 are pressed against each other, the coat of the electric wire 114 is disposed between the second pressing pieces 113, and then the second pressing pieces 114 are pressed against each other to electrically connect and fix the electric wire 114 to the combining part 110.

Of course, the metal wire of the electric wire 114 can be disposed between the first pressing pieces 112 and the second pressing pieces 113 and then the first and second pressing pieces 112 and 113 can be pressed against each other to electrically connect and fix the electric wire 114 to the combining part 110. However, the wire 114 can be fixed to the combining part 110 more securely by pressing and fixing even the coat of the electric wire 114.

An end of the electric wire 114 constructed as above is connected to the combining part 110 and the convex portion 102 of the body 101 of the snap electrode is fitted in the combining part 110 to which the electric wire 114 is connected and fixed. Then, the body 101 can be easily attached/detached to/from the combining protrusion 121 (shown in FIG. 5) of the pad 120, as shown in FIG. 4.

Figure 2:
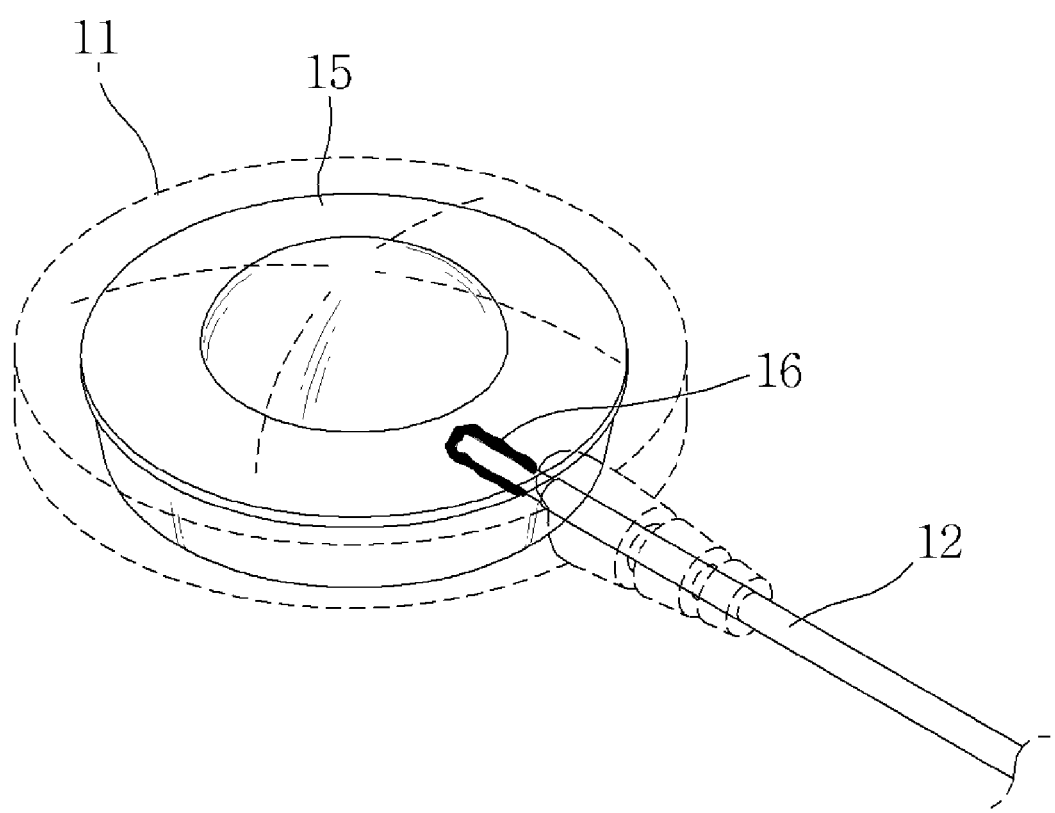
FIG. 2 is a perspective view of a conventional snap electrode.

Here, it is preferable to cover the body 101 with a case (not shown) that is extrusion-molded using a synthetic resin to construct a terminal such that the body 101 and the wire connecting part 116 are not exposed to the outside, as shown in FIGS. 1 and 2.

As described above, embodiments do not perform welding harmful to the human body to connect the electric wire 114 to the snap electrode for medical purposes and press-fixes the electric wire 114 to the combining part 110 and fixes the combining part 110 to the terminal body 101. Accordingly, the electric wire 114 can be securely connected to the snap electrode, the connecting structure does not harm the human body, and a cumbersome welding process is not needed so as to improve productivity.

Figure 5:
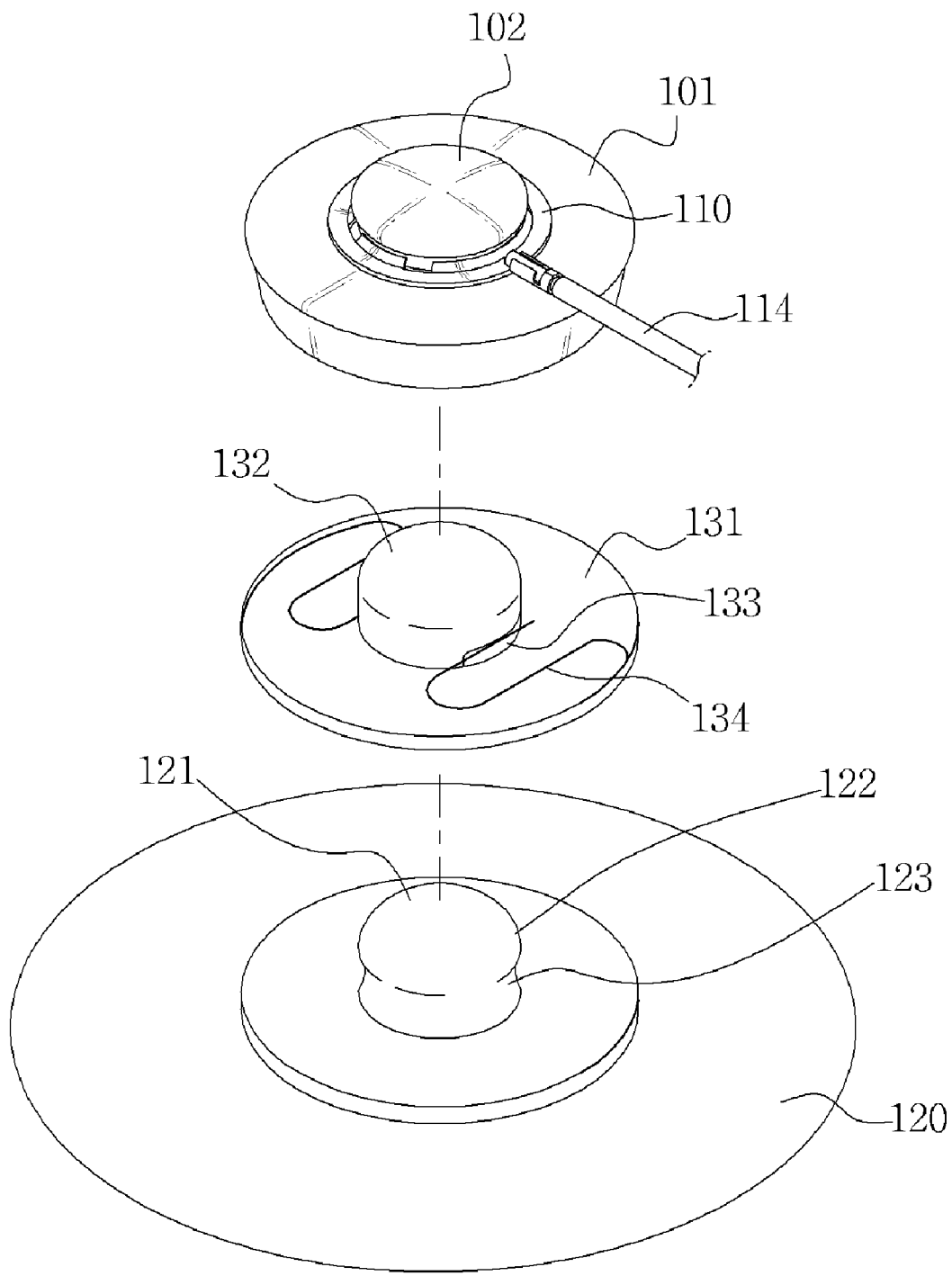
FIG. 5 is an exploded perspective view of the snap electrode according to an embodiment.
Figure 6:
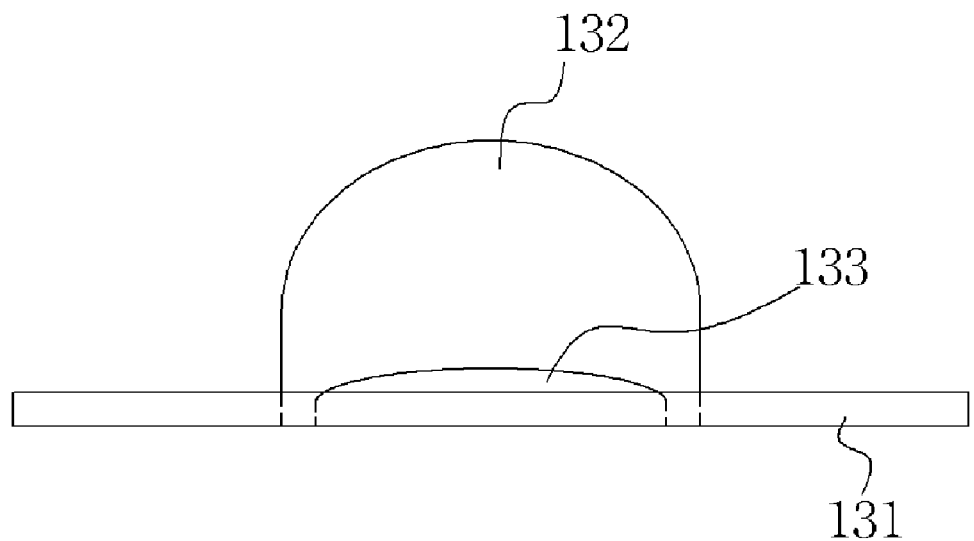
FIG. 6 is a side view of a base of the snap electrode.

FIG. 5 is an exploded perspective view of the snap electrode according to an embodiment and FIG. 6 is a side view of a base of the snap electrode.

Referring to FIG. 5, the snap electrode includes a base 131 for fitting the combining protrusion 121 of the pad 120 into the body 101. The base 131 includes a protrusion housing 132 into which the combining protrusion 121 of the pad 120 is inserted, spring slits 133 respectively formed at both sides of the protrusion housing 132 by cutting, and press springs 134 supported by the edge of the base 131 and inserted into the spring slits 133. The protrusion housing 132 is formed at the center of the base 131 and protruded upward. The spring slits 133 are formed by cutting both sides of the protrusion housing 132.

A retaining groove 123 is formed on the circumference of the combining protrusion 121 of the pad 120. When the combining protrusion 121 is inserted into the protrusion housing 132, the press springs 134 partially projected into the inside of the protrusion housing 132 through the spring slits 133 press the retaining groove 123 of the combining protrusion 121, and thus the pad 120 and the snap electrode are combined with each other.

When the retaining projection 122 of the combining protrusion 121 is inserted into the protrusion housing 132 to combine the snap electrode with the pad 120, the press springs 134 come out to the outside through the spring slits 133 formed at the protrusion housing 132 and then they are inserted into the protrusion housing 132 through the spring slits 133 and fitted in the retaining groove 123 of the combining protrusion 121. Here, the press springs 134 may be caught by upper cut faces of the spring slits 133, and thus the press springs 134 cannot press the retaining groove 123.

To solve this problem, the upper cut faces of the spring slits 133 are formed in a curved shape, as shown in FIG. 6, to prevent the press springs 134 from being caught by the upper cut faces of the spring slits 133. Accordingly, the snap electrode can be smoothly combined with the pad 120.

The connecting structure of the snap electrode for medical purposes and the electric wire according to embodiments have been explained.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A connecting structure of a snap electrode for medical purposes and an electric wire, comprising:
    a body on which a convex portion comprising a groove formed on the circumference thereof, in which a combining part is fitted, is formed;
    a base comprising a protrusion housing formed at the center thereof and spring slits formed at both sides of the protrusion housing, into which press springs are inserted; and
    the combining part comprising a ring shape and comprising a predetermined number of elastic fixing pieces protruded from the inner side thereof and a pair of first pressing pieces protruded from one side thereof and combined with the electric wire.

2. The connecting structure of a snap electrode for medical purposes and an electric wire of claim 1, wherein the elastic fixing pieces are bent upward at a predetermined angle or curved with a predetermined curvature.

3. The connecting structure of a snap electrode for medical purposes and an electric wire of claim 1, further comprising second pressing pieces formed at one side of the combining part configured to press and fix a coat of the electric wire.

4. The connecting structure of a snap electrode for medical purposes and an electric wire of claim 1, further comprising a case covering the body such that the body and a wire connecting part are not exposed to the outside.

5. The connecting structure of a snap electrode for medical purposes and an electric wire of claim 1, wherein upper cut faces of the spring slits formed at both sides of the protrusion housing are cut in a curved shape.

6. A method of forming a connecting structure of a snap electrode for medical purposes and an electric wire, the method comprising:
    forming a body on which a convex portion comprising a groove on the circumference thereof, in which a combining part is fitted;
    forming a base comprising a protrusion housing at the center thereof and spring slits at both sides of the protrusion housing, into which press springs are inserted; and
    forming the combining part comprising a ring shape and comprising a predetermined number of elastic fixing pieces protruded from the inner side thereof and a pair of first pressing pieces protruded from one side thereof and combined with the electric wire.

7. The method of claim 6, wherein the elastic fixing pieces are bent upward at a predetermined angle or curved with a predetermined curvature.

8. The method of claim 6, further comprising forming second pressing pieces at one side of the combining part configured to press and fix a coat of the electric wire.

9. The method of claim 6, further comprising forming a case covering the body such that the body and a wire connecting part are not exposed to the outside.

10. The method of claim 6, wherein upper cut faces of the spring slits at both sides of the protrusion housing are cut in a curved shape.

* * * * *